United States Patent [19]

Andresen et al.

[11] Patent Number: 4,705,616
[45] Date of Patent: Nov. 10, 1987

[54] ELECTROPHORESIS-MASS SPECTROMETRY PROBE

[75] Inventors: Brian D. Andresen, Pleasanton; Eric R. Fought, Livermore, both of Calif.

[73] Assignee: Sepragen Corporation, San Leandro, Calif.

[21] Appl. No.: 906,847

[22] Filed: Sep. 15, 1986

[51] Int. Cl.[4] .................. G01N 24/00; G01N 24/04; G01N 27/26; H01J 49/00
[52] U.S. Cl. ........................ 204/299 R; 204/180.1; 436/173; 250/288
[58] Field of Search ............ 204/180.1, 299 R; 436/173; 250/288 R, 288 A

[56] References Cited

PUBLICATIONS

José A. Olivares et al., "On-Line Mass Spectrometric Detection for Capillary Zone Electrophoresis" *Analytical Chemistry*, vol. 59, No. 8, Apr. 15, 1987.

Primary Examiner—John F. Niebling
Assistant Examiner—John S. Starsiak, Jr.
Attorney, Agent, or Firm—Shyamala T. Rajender

[57] ABSTRACT

The invention involves a new technique for the separation of complex mixtures of chemicals, which utilizes a unique interface probe for conventional mass spectrometers which allows the electrophoretically separated compounds to be analyzed in real-time by a mass spectrometer. This new chemical analysis interface, which couples electrophoresis with mass spectrometry, allows complex mixtures to be analyzed very rapidly, with much greater specificity, and with greater sensitivity. The interface or probe provides a means whereby large and/or polar molecules in complex mixtures to be completely characterized. The preferred embodiment of the probe utilizes a double capillary tip which allows the probe tip to be continually wetted by the buffer, which provides for increased heat dissipation, and results in a continually operating interface which is more durable and electronically stable than the illustrated single capillary tip probe interface.

28 Claims, 8 Drawing Figures

ELECTROPHORESIS-MASS SPECTROMETRY PROBE

BACKGROUND OF THE INVENTION

The invention described herein arose in the course, or under, Contract No. w-7405-ENG-48 between the United States Department of Energy and the University of California.

The invention relates to the separation, characterization and identification of complex mixtures of chemicals, particularly polar and/or large molecular weight and biological compounds, and more particularly to an electrophoresis-mass spectrometer interface probe for accomplishing such separation, characterization and identification.

Current trends in the analysis of complex mixture often utilize chromatographic separations, more specifically gas chromatographic (GC) columns interfaced directly with the ionization chamber of the mass spectrometer (MS). In this GC-MS combination, the eluants from the gas chromatographic (GC) column are directed into the ionization chamber of the mass spectrometer for ionization and analysis. High performance liquid chromatograph (HPLC)-mass spectrometry (MS) systems have also been developed for directing the HPLC eluant into the ion source of the MS. Although both GC-MS and HPLC-MS methods are powerful in their separation and ionization capabilities, it is not always possible to analyze all types of samples of complex mixtures with these systems. This is particularly true for the separation and characterization of polar and biological compounds in body fluids and other fluids of biological interest.

The identification of complex biological and polar compounds, such as specific proteins and amino acids, has currently been the focus of much research on abnormal cell growth and development. Current methods for the characterization of complex mixtures of large and polar molecules include gel or zone electrophoretic techniques. Electrophoretic separations are based on the differential migration of compounds in a conducting gel or other medium which is subject to an electrical potential. Electrophoretic techniques are known in the art and are exemplified by the publications listed.

"Zone Electrophoresis in Open-Tubular Glass Capillaries", J. W. Jorgensen et al., *Anal. Chem.*, 53, 1298-1302 (1981).

"Zone Electrophoresis in Open-Tubular Capillaries", J. W. Jorgenson, *Trends in Analytical Chemistry*, Vol. 3, No. 2, 1984.

"Electrokinetic Separations with Micellar Solutions and Open-Tubular Capillaries", S. Terake et al., *Anal. Chem.*, 56, 113-116 (1984).

Electrophoretic techniques can provide very clean separations of many types of complex molecules in biological matrices. This type of analysis has been utilized routinely for the separation and characterlzation of proteins, amino acids, enzymes, DNA, RNA, plasmids, drugs, toxins and a host of other substances in body fluids, environmental samples and in other fluids of biological interest. While the separation of complex and polar compounds by gel electrophoresis is a highly reliable and cost-effective analytical approach, and while the separation of macromolecules by gel electrophoresis appears routine, this technique does not uniquely identify or characterize individual compounds and does not provide for structure elucidation. Typically, an electrophoretic chromatogram or electropherogram produces only spots, bands or locations of compounds. The separated material (electrophoretic bands) must be separately prepared for identification using a variety of other techniques such as transfer and staining techniques which are often cumbersome and costly. The identification of a specific compound can only made by comparison to known standards. More recent trends in electrophoretic techniques utilize open tubular columns, which require derivatization, labeling or tagging of the compounds of interest. The individual derivatized, labeled or tagged components are then separated by electrophoresis and detected by means of any externally located, or on-line detection device such as a fluorescence or absorption detector. Although this approach is sensitive, it is not specific and the compounds of interest are not uniquely identified. Dissimilar compounds with identical migration rates cannot be differentiated. Thus, the technique of electrophoresis suffers from certain drawbacks some of which are summarized below.

It requires a slow and detailed gel preparation step which can be manually intensive and the generation of satisfactory gels requires experienced personnel. The gels can also be toxic to humans and therefore, poses a health hazard.

There is also a requirement for good temperature control of the gels. Heated gels typically yield poor chromatograms, making pattern recognition difficult.

The procedure has not been generally automated.

The analysis always requires standards. Often standards are not available and many of the electrophoretic bands, therefore, remain unidentified.

It requires a staining step for the visualization of the electrophoretic bands. The visualization step often requires considerable time and can be very tedious, and the analysis requires many hours to complete.

More recently it was discovered that when a high voltage is applied to a long narrow bore capillary tube, made of glass or quartz, an electrophoretic separation of organic and inorganic compounds can be performed (see article in *Anal. Chem.* 53, 1298 (1981) cited earlier. When a fluorescence detector is placed in series (on line) with the Capillary tube, fluorescent compounds can be detected as they migrate from the anode to the cathode of the capillary system. Tests have shown that the capillary electrophoretic separation technique provides a better qualitative and quantitative analysis. While this new capillary electrophoresis technique is being utilized for the separation and characterization of complex mixtures, there are still some problems associated with this modified electrophoretic technique. The technique suffers from poor detection sensitivity. Most compounds must be first chemically reacted with a fluorescent dye prior to the capillary electrophoretic analysis in order to identify them by means of the fluorescence detector. Many chemicals do not react with the fluorescent dye and are, therefore, not amenable to analysis using the technique.

As with all chromatography, a compound can only be identified by comparisons to known standards utilizing a variety of cumbersome techniques. No other information concerning exact molecular weights, structure, or formula can be obtained from this type of analysis on a completely unknown sample.

It is thus seen that although zone or capillary electrophoresis is a marked improvement over gel electrophoresis in some respects, problems still exist in the wide applicability of even capillary electrophoresis. Some of the disadvantages of the prior art methods are highlighted herein below.

The derivatized or tagged compounds analyzed and detected are not in the same form as the initial compounds isolated in the analysis and identified. Preliminary derivatization steps are needed to generate fluorescent analogs. Only the fluorescent chromophores, and not the parent compounds, are detected by the capillary electrophoresis technique. In addition, no other significant chemical data related to the characterization and identification of the compounds are generated during the analysis. The compounds which are isolated from gels are significantly contaminated with the electrophoretic polymers.

Mass spectrometry, on the other hand, has proven itself to be an extremely valuable tool in a variety of complex analyses such as the identification and quantification of causative toxic agents in drug overdose cases, the analysis of environmental toxins and pollutants, and the structure elucidation of many new biologically significant compounds. Mass spectrometry can now achieve high mass resolution and routinely record molecular weights of over 12,000. This instrumental method has been very useful in the characterization of compounds because it can yield more analytical data per microgram of sample than most other instrumental methods of analysis. The mass spectrometer is a very sensitive instrument, with routine detection limits in the range of $10^{-12}$ to $10^{-9}$ gms and in some instances, even with lower detection limits of the order of $10^{-15}$ gram. It is very specific in the type of data that can be generated, and it can generate molecular weight and structural information concerning the compounds analyzed and identified.

However, the technique of mass spectrometry at the present time, is not very suitable for the analysis of polar or high molecular weight compounds in complex mixtures. In addition, the sensitivity limits of mass spectral analyses can only be achieved if the samples prepared for analysis are highly purified. Only when a plurality of mass spectrometers, connected in a tandem fashion, can even attempt the separation and identification of complex mixtures. Therefore, before useful or meaningful data can be generated using mass spectral analysis for the characterization of polar or large molecular weight compounds in complex mixtures, a chromatographic or electrophoretic separation of the mixture into relatively pure components needs to be performed first. Secondly, the compound to be analyzed must be amenable to ionization in a vacuum such as that encountered in the ionization chamber of a mass spectrometer.

Thus, a need exists in the art for a method of analysis, particularly for complex mixtures, which does not require fluorescent labels or tags, operates in real time, and yields molecular weights, formula, fragmentation data and structural information about the compounds initially separated by capillary electrophoresis or chromatography. Since it is most desirable to have individual compounds separated by electrophoretic techniques, and have the separated compounds analyzed and identified by procedures tnat are both sensitive and specific, it would be most reasonable to utilize a mass spectrometer as a detector to generate specific molecular weight data or unique fragmentation information. Such an analytical approach would not require derivatization and/or transfer steps and would provide a more complete method of analysis. The desirability of the combination of gel electrophoresis and mass spectrometry has been broadly alluded to in the article "Mass Spectrometry of Large, Fragile, and Involatile Molecules", K. L. Busch et al., Science, Vol. 218, 247–254 (15 Oct. 1982).

While the desirability of the combination of electrophoresis (EP) and mass spectrometry (MS) has been recognized in the art, there has been no development of a suitable or satisfactory method for such combination and a need still exists for an EP-MS interface whicn provides for real-time analysis of compounds separated by gel or capillary electrophoresis. Such an EP-MS interface must satisfy and meet some stringent requirements in order to operate satisfactorily for its intended purpose.

Because a mass spectrometer operates most effectively at or below pressures of $10^{-5}$ Torr, an EP-MS interface must not compromise tne vacuum integrity of the mass spectrometer. The EP-MS interface must be capable of guiding and directing the compounds initially separated by gel or capillary electrophoresis directly into the ion chamber of the mass spectrometer.

Furthermore, since capillary electrophoresis separations are carried out in the range of 10,000–30,000 volts, the entire EP-MS system must "float" relative to the ground potentials of the mass spectrometer in order to maintain the focus of the mass spectrometer's ion optics.

In view of the small volume capacity of the capillary tube of the electrophoresis system, an appropriate sample introduction system that can, not only operate in the high voltage environment of the EP system, but which also provides for sufficient sample size suitable for MS analysis is considered to be necessary.

The entire EP-MS interface should be self contained, portable and easily transferable from one type of mass spectrometer to another without much modification of the mass spectrometer or inlet systems or vacuum pumps.

Therefore, it is an object of this invention to provide a method of analysis of complex mixtures of chemicals.

A further object of the invention is to provide a technique for the separation and identification of complex mixtures of chemicals utilizing zone electrophoresis and mass spectrometry.

Another object of the invention is to provide a method of analysis which not only utilizes the sensitivity and specificity of mass spectrometry as a detector for capillary electrophoresis, but which also operates in real time, and yields molecular weights, formula, fragmentation and structural information about the compounds subjected to capillary electrophoresis.

Yet another object is to provide an electrophoresis probe that is capable of being inserted directly into the ion source of a mass spectrometer.

Another object of the invention is to provide an electrophoresis-mass spectrometer (EP-MS) interface which provides for real-time analysis of compounds separated by capillary electrophoresis.

Another object of the invention is to provide an EP-MS interface which maintains vacuum integrity required for mass spectrometry.

Another object of the invention is to provide an EP-MS interface which is capable of operation under required high voltage and vacuum conditions.

Another object of the invention is to provide an EP-MS interface which includes a sample introduction system with a sufficient volume capacity to maintain operation of the mass spectrometer.

Another object of the invention is to provide an EP-MS interface which is self contained and readily transferred to different mass spectrometers, to provide for high resolution or low resolution mass spectral analysis.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects and in accordance with the purpose of the present invention as embodied and broadly described herein, the instant invention is directed to an electrophoresis-mass spectrometer (EP-MS) interface which utilizes an insertion probe that allows the electrophoretically separated and resolved compounds to be analyzed in real-time by a mass spectrometer or detected and identified by other means such as a fluorescence or absorption or radiation detector. This interface for chemical and biochemical analysis, which couples electrophoresis with mass spectrometry, allows components of complex mixtures to be analyzed very rapidly, with much greater specificity ano with greater sensitivity.

The EP-MS interface of this invention utilizes a probe which includes a capillary column as the electrophoretic separator and which can be inserted directly into the ion source of any commercial mass spectrometer or can be plugged into other detection devices as mentioned earlier. The probe basically comprises at least one capillary tube with high thermal conductivity walls, a suitable heat sink for the capillary, an S-type capillary sampling inlet, and a wall coating of a non-ionic hydrophilic polymer, to suppress peak tailing, and is driven by a 20–30 kV potential difference. One end of the electrophoretic tube is open to the atmosphere (and is at atmospheric pressure) and the other end is inserted or adapted to be inserted into the ion source of the mass spectrometer or other detection devices. One embodiment of the interface probe utilizes a single capillary which can be used for single runs or for intermittent use. Another embodiment uses a double capillary arrangement which is suitable for continuous operation.

Compounds to be analyzed are injected into the sample inlet, or port of the probe and then allowed to migrate towards the ion source. As the individual compounds reach the ion source and the open end of the electrophoretic capillary, they are ionized by bombardment with an ionizing beam such as fast atom, electron or photon bombardment guns or by surface ionization or by electrospray ionization or by other ionizing techniques known in the art of mass spectrometry. This technique yields molecular ions and mass spectral fragmentation data for compounds that are not normally amenable to routine mass spectral analyses. Highly specific data are obtained concerning the molecular weights of individual compounds as also their characteristic fragmentation data. Each electrophoretic component is thus detected and identified in detail in real-time.

The EP-MS interface of this invention provides for rapid chemical analyses of complex mixtures of biological and other polar compounds, and is thus beneficial to the biomedical and the biotechnology community as well as to analytical, clinical and research laboratories. The instant probe may be used with existing mass spectrometers and does not require any major modification of existing equipment. The probe of this invention also enables electrophoretic separations directly in the ion source of a mass spectrometer where they can be substantially simultaneously analyzed by the mass spectrometer.

The electrophoresis interface probe of this invention is a compact portable, integral electrophoresis unit which can be used in field operations as a stand-alone, portable compact unit for carrying out electrophoretic separations or may be used in the laboratory in combination with other analytical and/or detection devices.

DETAILED DESCRIPTION OF THE INVENTION

The present invention is directed to a method and apparatus for performing electrophoresis directly in the ion source of a mass spectrometer. As a result of this invention, biological, inorganic and organic chemicals which are separated from complex mixtures by the electrophoretic process can be analyzed in real-time by a mass spectrometer to yield molecular weights and structural information and unique identification of the compounds. This invention utilizes a mass spectrometer as a detector for compounds separated by electrophoresis and offers an entirely new dimension to electrophoresis. The apparatus of this invention includes an interface probe which is chemically inert, is a good conductor of heat as well as a good electrical insulator. The invention is useful in characterizing large biological and/or polar molecules, particularly in the separation and identification of polar and/or biological compounds, such as nucleic acids, proteins, amino acids, and polyfunctional phenols and steroids, in complex mixtures. The interface probe of this invention contains an electrically conducting polymer gel or buffer capable of withstanding a high voltage and of sustained operation under such high voltage conoitions.

Basically, the electrophoretic interface probe of this invention, in one embodiment, uses at least one microcapillary tube with high thermal conductivity walls, a heat sink, an S-type capillary sampling inlet, and a wall coating of a nonionic hydrophilic polymer to suppress peak tailing, and is driven by a 20–30 kV potential difference. One end of the electrophoretic tube of the probe is be at atmospheric pressure and the other end is inserted into the ion source of a mass spectrometer. Compounds to be analyzed are injected into the sample injection port or inlet of the probe and then allowed to migrate towards the ion source of the mass spectrometer. As the individual compounds reach the ion source and the open end of the electrophoresis probe, they are ionized by known ionizing techniques such as fast atom, electron or photon bombardment or electrospray ionization and the like. These ionization and identification techniques yield molecular ions and mass spectral fragmentation data for compounds that are normally not amenable to routine mass spectral analyses. In this manner, highly specific data can be obtained concerning the molecular weights of individual compounds along with characteristic fragmentation data. Each electrophoretic component can thus be identified in detail and in real-time by the mass spectrometer.

The interface probe of this invention may be used, for example, to separate compounds in blood, serum and urine and other biological fluids and allow for the characterization of unusual amino acids, proteins, hormones and other compounds that may point to human disease. The interface can, simultaneously, analyze organic and inorganic compounds. The EP-MS interface of this invention is a major advance in the biotechnology area and would be beneficial in a variety of scientific, biotechnical and medical applications.

Figure 1:
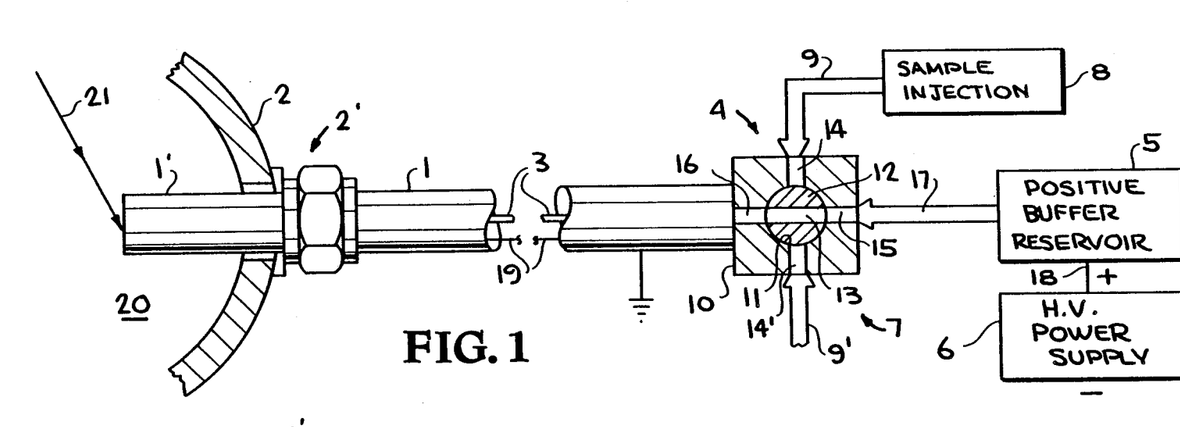
FIG. 1 illustrates an embodiment of a single capillary electrophoresis-mass spectrometer interface probe, made in accordance with the present invention.
Figure 2:
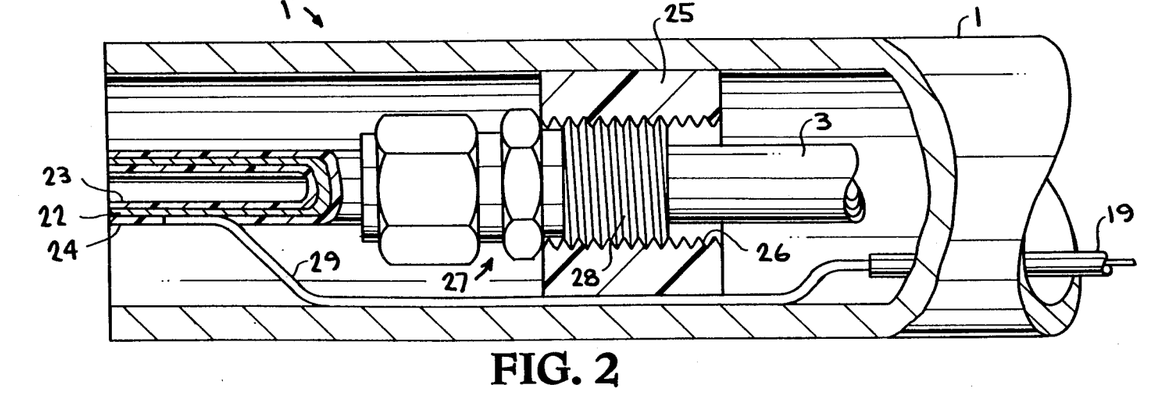
FIG. 2 is an enlarged view of the probe tip of FIG. 1.

The preferred embodiment of tne invention, illustrated in FIGS. 3–7, utilizes a double capillary interface probe and provides for continuous operation, while the embodiment of FIGS. 1 and 2 utilizes a single capillary interface probe for single runs or for intermittent operation.

Referring now to FIGS. 1 and 2, the single capillary EP-MS interface probe basically comprises a casing or housing 1 having a tip section 1' located within a mass spectrometer 2 and secured thereto by a coupling mechanism 2'. Capillary tube 3 extends through casing 1, a sample introduction mechanism generally indicated at 4, a buffer reservoir 5, and a high voltage power supply 6. Sample introduction mechanism 4 includes a multi-port value 7 and a sample injection arrangement or source 8 connected to valve 7 by line, tube or conduit 9, valve 7 being illustrated in enlarged cross-section. Valve 1 comprises a housing 10 having a chamber 11 therein in which a rotatable member 12 is positioned, member 12 having a passage 13 extending therethrough. Housing 10 is provided with four ports or passages 14, 14', 15 and 16 with port 14 being connected to tube 9 from source 8, and port 14' being connected to a line, tube or conduit 9', which may be connected to an additional monitoring or detection device, such as a fluorescence or absorption detector to continually monitor the sample being analyzed, or may be connected to a disposal means for the excess sample. Port 15 is connected to a line, tube or conduit 17 which is connected to buffer reservoir 5, and port 16 is connected to capillary tube 3. The rotatable valve member 12 is connected to an activation and timing mechanisms, not shown, for rotating member 12 at a selected interval between the position shown where passage 13 is aligned with ports 15 and 16 for allowing buffer material or fluid from reservoir 5 to pass into capillary tube 13, to a position where passage 13 is aligned with port 14 which allows the passage 13 to filled with sample material from injection means or source 8. When the passage 13 is filled with sample material the valve member 12 is rotated to tne position shown whereby the sample material in passage 13 is mixed with buffer material from reservoir 5, and undergoes the electrophoresis process as it migrates down capillary tube 3.

Electrical energy for the electrophoresis process is supplied by power supply 6 (20–30 kV) with a positive terminal thereof connected by an electrical lead 18 to buffer reservoir 5. An electrical lead or return line 19 is connected to the negative terminal of power supply 6 via a grounded connection 29 shown in FIG. 2. Return electrical lead 19 is electrically connected to capillary tube 3 as shown and described below in reference to FIG. 2.

Components of the sample material from source 8, after undergoing the electrophoretic separation as it migrates down capillary tube 3 reach the probe tip section 1' of casing 1 in a chamber 20 of mass spectrometer 2. As the components reach the probe tip they are bombarded by an ionizing beam 21 such as that from a fast atom bombardment (FAB) gun for ionizing the components. The ionized components are then analyzed in the mass spectrometer 2, as is known in the art. The beam 21, which may be composed of xenon gas, for example, is preferably directed onto the discharging components from probe tip 1' at an angle between 45° and 90°, more preferably about 26°. Coupling mechanism 2' provides a vacuum tight connection between casing 1 and mass spectrometer 2 and may be of the type illustrated in the embodiment of FIG. 6.

FIG. 2 illustrates an enlarged view of the probe tip 1' of casing 1. Capillary tube 3 in this embodiment is of a multi-layer configuration consisting of a central tube 22, an inner layer 23, and an outer layer 24. Central tube 22 is constructed of quartz, sapphire, glass, or ceramic, for example, having an internal diameter of about 10 to 100 mils and wall thickness of about 0.1 inch to about 0.5 inch. Inner layer 23 is composed of polysilylether, polyethyleneglycol, or carbowax covalently bonded to central tube 22 and has a thickness of about $0.1\mu$ to $0.5\mu$. Outer layer 24 is constructed of polyacrylamide, polyethylene or polystyrene, having an outer diameter of about 0.1 inch to 0.25 inch and thickness of about 0.01 inch to 0.5 inch. Layers 23 and 24 may be formed integrally on central tube 22. For example, a conducting metal tip may be formed at the probe tip by coating the tip with a conducting coating made of silver nitrate, dilute ammonia solution and glucose. A contact spring which touches the conduction film enables the passage of current around and into the center of the capillary. The layers 23 and 24 function to "float" the entire probe with respect to the ground potentials of the mass spectrometer. Because sleeve 25 (see FIG. 2), is nonconducting, any current passing through the tip of the electrophoretic probe or capillary parts 22, 23, or 24, will not affect the focus of the mass spectrometer's ion optics.

Capillary tube 3 is secured within probe casing tip 1' by a nonconducting block or member 25 constructed of materials like polystyrene, teflon or polycarbonate, having a threaded aperture 26 therethrough. An air tight coupling mechanism generally indicated at 27 is positioned around capillary tube 3 and includes a threaded member 28 which is screwed into aperture 26 of block 25. An electrical return lead or wire 29 is connected at one end to the central tube 22 of capillary tube 3 and at the opposite end to return lead 19. Return lead 19 is preferably of a flat configuration.

To assemble the probe tip 1' as shown in FIG. 2, the coupling mechanism 27 is slid over the end of capillary tube 3 and the threaded member 28 is screwed into block 25. Thereafter return lead 29 is secured to capillary tube 3, and the assembly (tube 3, block 25, coupling 27 and return lead 29) is then positioned to be inserted into casing tip 1'. Prior to inserting the assembly into casing 1, an inner surface of casing 1 at which block 25 is to be located, is covered with adhesive sealant, such as bonding material, quick setting cement or super glue, and upon inserting the assembly into casing 1 in the location desired, the adhesive sealant functions to secure the block 25 in place and provides a vacuum tight seal between block 25 and casing 1. If desired, the block 25 may be provided with a slot into which return lead or wire 29 is snugly positioned and sealed by an adhesive sealant.

While the single capillary electrophoresis system of FIG. 1 works well for single runs or for intermittent operation, it has to be reconditioned each time an analysis is performed because the tip of the capillary tube is likely to heat up and dry out, because the probe tip gets very close to the ion source of the mass spectrometer where the ion source is generally heated to about 200° C. or higher. Furthermore, bombardment of the tip with energetic xenon gas contributes additionally to the heating effect and raises the temperature of the probe tip. When the buffer and polymer at the end of the probe tip became too hot, there can be a loss of electrical conduction, and consequently, a lower or diminisned current flow and a breakdown of the electrophoresis process. As a result, the single capillary probe interface FIG. 1 served satisfactorily for single runs or intermittent operation, but is not particularly convenient or suitable for continuous, long term (of the order of hours to days) operation. Interfaces of this type can, however, be manufactured inexpensively, and thus can be discarded after a single run.

The double capillary EP-MS interface probe of FIGS. 3–7 overcomes the problems of the embodiment of FIG. 1, and provides for continuous operation. This double-feed-line approach allows for the capillary electrophoresis probe tip to be continually wetted by the buffer. This, in turn, allows for increased heat dissipation, and results in a continually operating interface which is more durable and electrically stable. As described below, the double capillary probe tip includes a "cell" located near the end and within the mass spectrometer and thus is subjected to the heat from the ion source as well as the heat generated by fast atom or electron bombardment. A variety of materials are suitable for the construction of the "cell". These include but are not limited to teflon, polyvinyl chloride (PVC), inert polymer-coated stainless steel, glass, polyethylene, Viton, polycarbonate, and combinations of these material. Polycarbonate is preferred because of its strength, electrical insulation capabilities, and ability to be easily machined into small parts. The probe tip has a diameter of about 0.5 inch and length of about 1.0 inch, for example, with the probe having an overall length of about 20 to 30 inches.

Figure 3:
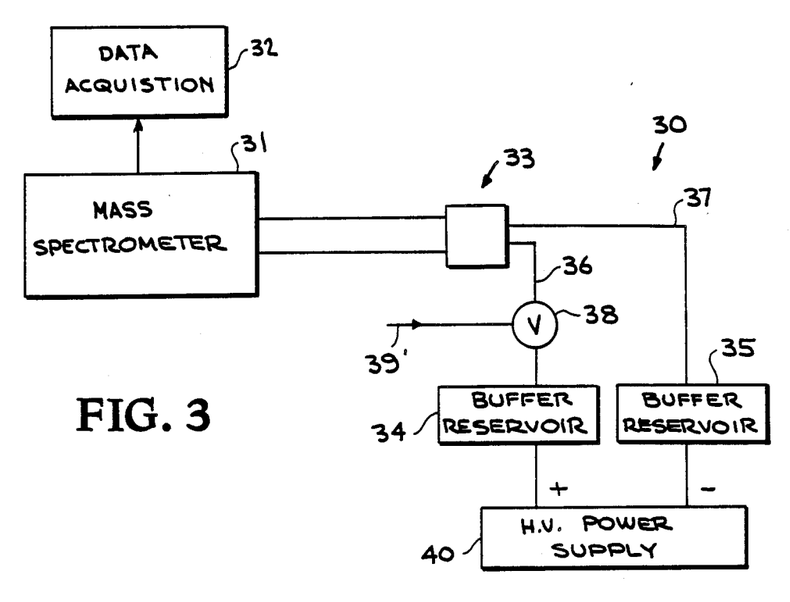
FIG. 3 is a block diagram of an overall electrophoresis-mass spectrometry system using a double capillary arrangement in accordance with the present invention.

Referring now to the drawings, FIG. 3 illustrates an overall EP-MS system made in accordance with the invention and utilizing a double capillary interface probe. The EP-MS system comprises an electrophoresis interface probe apparatus generally indicated at 30, which is connected to a mass spectrometer 31 the output of which is fed into a data acquisition mechanism 32. The interface probe apparatus 30 includes a capillary interface probe, generally indicated at 33, connected to a mass spectrometer 31 and to which are connected a pair of buffer reservoirs 34 and 35 by capillary tubes 36 and 37, respectively with tube 36 having a multi-port valve 38 mounted therein, valve 38 also being connected to a sample injection means, source, port or inlet indicated at 39. The buffer reservoirs 34 and 35 are connected respectively to positive and negative terminals of a high voltage power supply 40. Valve 38 and sample injection means 39 cooperate to form a sample introduction system of this embodiment.

Figure 4A:
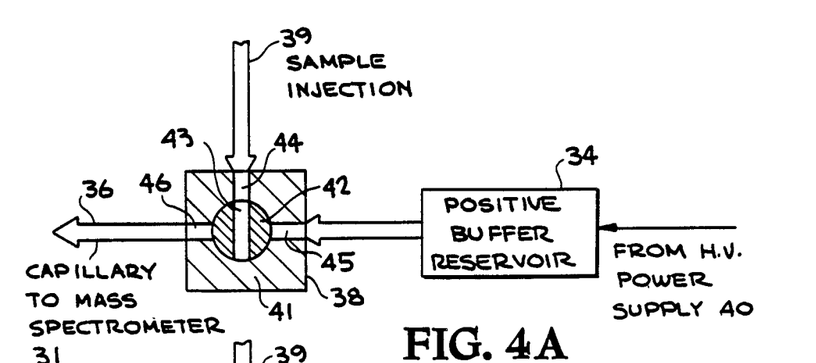
FIGS. 4A and 4B illustrate in partial cross-section the sample introduction system of the embodiment of the present invention illustrated in FIG. 3.
Figure 4B:
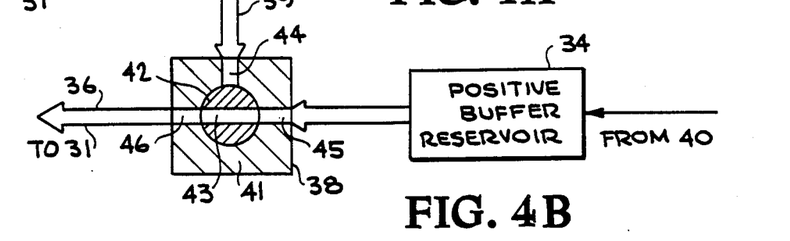

FIGS. 4A and 4B illustrate the operation of the sample introduction system, which is controlled by the operation of the valve 38. Valve 38 includes a body or housing 41 having therein a movable (rotatable) member 42 with a passage or chamber 43 therethrough. Valve housing 41 is also provided with three passages or ports 44, 45 and 46, passage 44 being connected to sample injection mechanism, port, inlet or source 39, passage 45 being connected to buffer reservoir 34, and passage 46 being connected to mass spectrometer 31 via probe tip 33. As shown in FIG. 4A, with valve member 42 turned so as to allow passage or chamber 43 to align with passage or port 44, a quantity of sample material to be analyzed is inserted into passage 43 from sample injection mechanism, port, inlet or source 39, thus filling passage 43 with the sample material. Rotation of the valve member 42, as shown in FIG. 4B aligns passage or chamber 43 with passages or ports 45 and 46, whereby the sample material in passage 43 is mixed with the buffer material from reservoir 34 and the electrophoretic separation process takes place as the sample material and buffer material migrate down the capillary tube 36. The amount of sample material from source 39 injected into capillary tube 36 is controlled by the rate of rotation or actuation of valve 38 or by the length of time the high voltage is applied to the sample. Valve 38 may be controlled by known timing and activating means, not shown.

By way example, the capillary tubes 36 and 37 may be constructed of quartz, sapphire, glass, ceramic or polyethylene, and may have an inner lining as described earlier in the embodiment of FIG. 1. For example, when a sample material from source 39 is a protein, and the buffer from reservoir 34 is 0.05N $KH_2PO_4$ in water, approximately 1 to 10 mg of sample material is directed into capillary tube 36 in a time period of about 15 seconds at an applied voltage of 7 KV.

Figure 5:
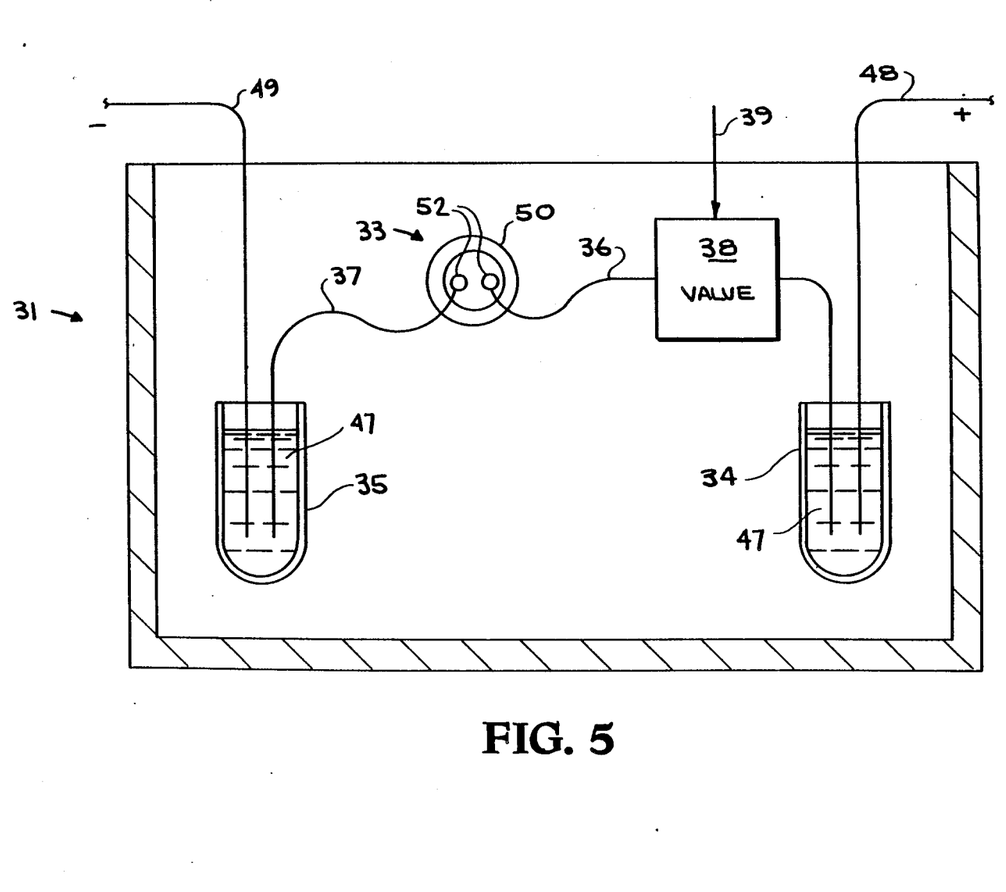
FIG. 5 schematically illustrates the relationship of the probe, the sample introduction system, and the buffer reservoirs of the system of FIG. 3.

FIG. 5 schematically illustrates the relationship between the high voltage power supply 40 buffer reservoirs 34 and 35, sample insertion system (valve 38 and injection means or source 39), capillary tubes 36 and 37, probe tip 33 and mass spectrometer 31, illustrated in block diagram in FIG. 3. As shown in FIG. 5, each of the buffer reservoirs 34 and 35 is filled with an electrically conducting buffer material or fluid 47, such as phosphate, citrate, or acetate buffers, or gel material known in the electrophoresis art. Buffer reservoir 34 is connected to a positive terminal of power supply 40 via an electrical lead 48, while an electrical lead 49 connects buffer reservoir 35 with a negative terminal of power supply 40. Probe tip 33 is mounted on mass spectrometer 31, as described and illustrated in detail hereinafter in reference to the embodiments illustrated in FIGS. 6 and 7.

Figure 6:
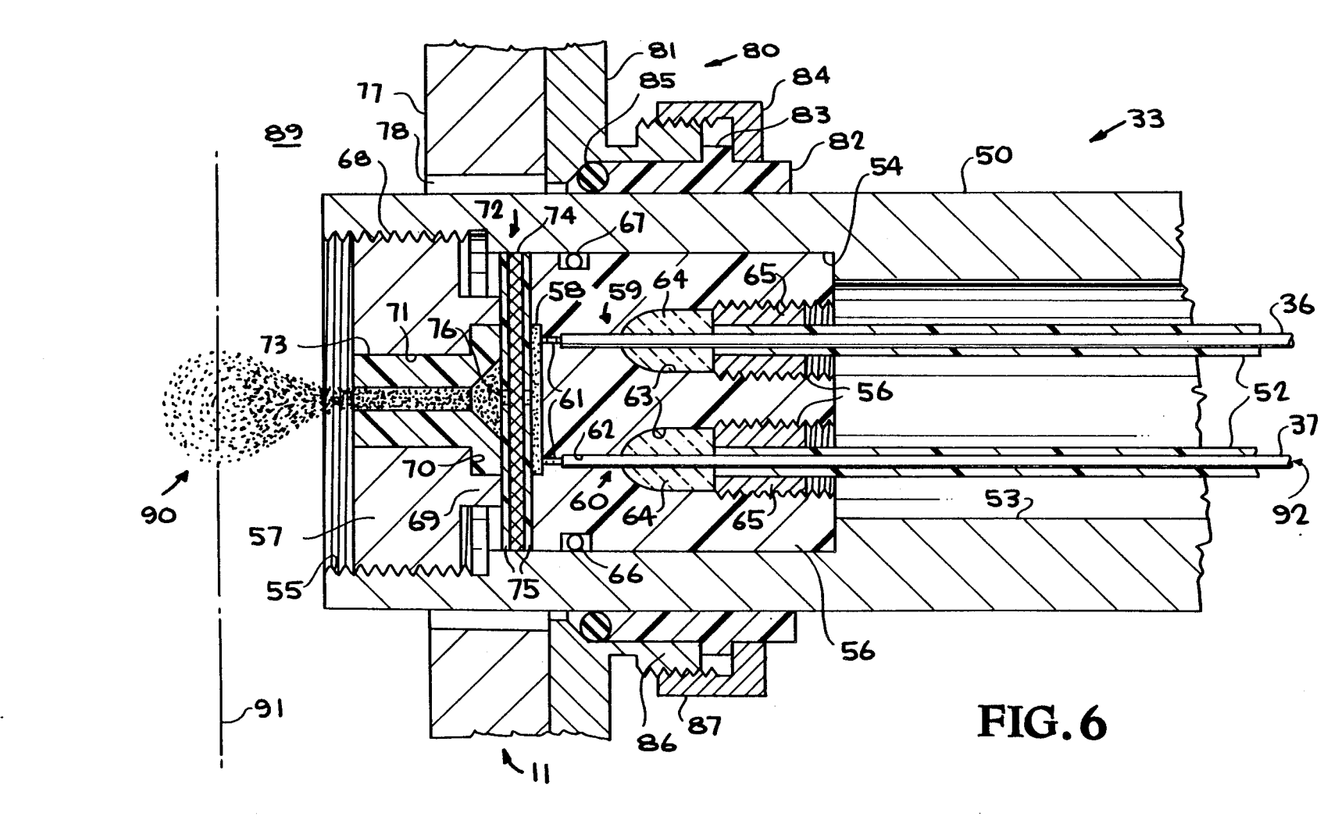
FIG. 6 is an enlarged view of an embodiment of the double capillary interface probe tip made in accordance with the invention.

An embodiment of the double capillary tube interface probe tip 33 is illustrated in FIG. 6, and is contained within a housing or casing 50, constructed of stainless steel, for example, with an outside diameter of about 0.5 inch. The capillary tubes 36 and 37 extend into casing 50 within electrical insulation sleeves 52, constructed of polyurethane or teflon, for example, with a wall thickness of, for example, about 0.25 inch. Housing or casing 50 is provided with a longitudinally extending opening having three different diameter sections 53, 54 and 55. A capillary terminal block 56 or "cell" discussed above is positioned in section 54 of casing 50, while a retainer and compression plug or member 57 is positioned in section 55 of casing 50.

Capillary terminal block or "cell" 56 is preferably constructed of polycarbonate and is provided with, for example, an elongated slit, groove, or countersink portion 58, having a width of about 0.1 inch to 0.25 inch, at one end thereof with a pair of spaced passageways 59 and 60 extending from the opposite end into slit or countersink 58, as seen in FIG. 6. Passageways 59 and 60 each is provided with three different diameter section 61, 62 and 63, with sections 63 having a tapered or curved inner portion and a threaded outer portion. Capillary tubes 36 and 37 extend through opening section 53 of casing 50, through sections 63 of passageways 59 and 60 and into sections 62, so as to terminate adjacent or fuse with sections 61 of the passageways. A pair of vacuum tight seals 64 are positioned in the curved end portions of passageways sections 63 and around capillary tubes 36 and 37. The seals 64 may be constructed of graphite or teflon or a similar durable material for example. The insulation sleeves 52 terminate in passageway sections 63 adjacent the seals 64 with the seals 64 being held in place by threaded, hollow, retainer members or plugs 65, which may be constructed to also retain the inner end of the insulation sleeves 52. Retainer members 65 may be constructed of stainless steel or sturdy plastic, for example. Capillary terminal block 56 is also provided with a groove 66 which extends around the periphery thereof and in which is located a seal member 67, such as an oversized O-ring, which provides a vacuum seal between the inner surface of casing section 54 and block 56. The elongated slit 58 in block 56 may be enlarged to an oval configuration, which would increase sensitivity but reduce resolution of the material components passing therethrough.

Retainer plug or member 57 is provided with external threads 68 which cooperate with threads on the casing opening section 55 for removably retaining plug 57 in casing 50. Retainer plug 57 includes a reduced cross-section protruding portion 69 having a countersink 70 therein which is connected to a centrally located opening 71 which extends through plug 57. Protruding portion 69 of plug 57 extends into casing opening section 54 and serves to retain a screen assembly, generally indicated at 72, in abutment with capillary terminal block 56. A nozzle 73, constructed of plastic or other suitable material, is positioned in countersink 70 and opening 71 of retainer plug 57 and abuts against screen assembly. The screen assembly 72 comprises a molecular screen or sieve 74 positioned between a pair of spacers or washers 75 having centrally located apertures 76. The molecular screen 74 may, for example, be constructed of teflon, paper, cellulose or polycarbonate, with a thickness of about 0.01 inch to 0.05 inch, with the washers 75 being constructed of teflon, paper or polycarbonate, having a thickness of about 50 mils to 100 mils, with the apertures 76 having a diameter of about 0.3 inch. The screen assembly 72 is pressed against the face or end of block 56 by retaining plug 57 being threaded into casing section 55 to produce a tight compression fit therebetween.

Mass spectrometer 31 includes a wall 77 having an opening 78 therein through which an end of probe tip casing 50 extends, as seen in FIG. 6. The casing 50 is retained in wall 77 by a coupling mechanism generally indicated at 80, which includes a collar or mounting member or bracket 81 constructed of stainless steel, for example, and secured to wall 77, by means not shown, such as by welding or screws; an electrical insulation sleeve or member 82, constructed of teflon or polycarbonate or a similar material for example, positioned around casing 50, sleeve 82 having a protruding section or ring 83; a seal nut or bracket 84 positioned around sleeve 82; and an O-ring 85 positioned around casing 50 intermediate mounting member 81 and sleeve 82. Mounting member 81 includes an outwardly extending flange portion 86 which fits around sleeve 82 and has an external threaded surface. Seal nut 84 includes an outwardly extending flange portion 87 having an internal threaded surface which cooperates with the threads on flange portion 86 of mounting member 81. Turning of the seal nut 84 onto the mounting member 81 contacts the protruding ring 83 of sleeve 82 forcing sleeve 82 toward O-ring 85 and mounting member 81, causing a vacuum tight seal between probe casing 50 and mass spectrometer wall 77 while mounting or securing casing 50 to wall 77.

In operation of the FIG. 6 probe tip 33, sample material indicated at 88 from source 39 of FIG. 1, which is separated into components in capillary tube 36 by the electrophoresis process, is directed from capillary tube 36 via passage 61 into slit 58 where it is vaporized, and then passes through opening 76 in a first washer 75, through molecular screen 74, opening 76 in the other washer 7, and through nozzle 73 into a chamber 89 of mass spectrometer 31, as indicated at 90. The components 90 of the sample material are struck by an energetic beam 91, of ionized xenon gas, for example, from a fast atom bombardment (FAB) gun, not shown.

To maintain continuous operation of the FIG. 6 probe tip negatively charged buffer material or fluid 47 from buffer reservoir 35 migrates through capillary tube 37 as indicated at 92 into passage 61 and slit 58. This prevents the tip or end of capillary tube 36 from heating up and drying out, as discussed above with respect to the single capillary probe tip of the FIG. 1 embodiment, thereby conduction through the buffer is maintained, current flow is not diminished and enables continual operation of the electrophoresis process. Also the negatively charged material passing through capillary 37 serves to complete an electrical circuit from and to power supply 40.

Figure 7:
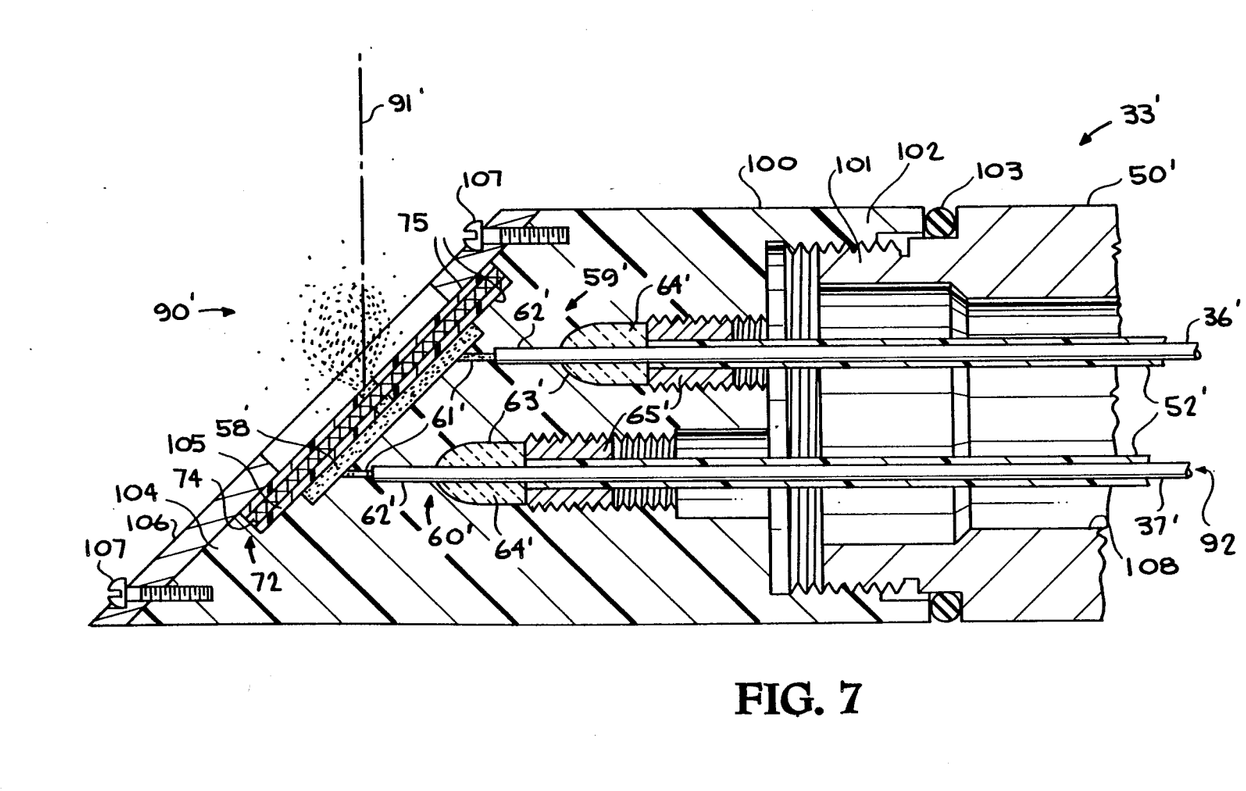
FIG. 7 illustrates another embodiment of the double capillary interface probe tip.

The embodiment of FIG. 7 differs from that of the FIG. 6 probe tip primarily in the construction of the end of the tip to enable an ionizing beam to impinge directly on the front face of the tip for ionizing the components of the sample material passing therethrough. wile not shown, a mounting or coupling mechanism similar to mechanism 80 in FIG. 6 may be secured to the FIG. 7 probe tip to secure the tip in a mass spectrometer. Where components similar to those of FIG. 6 are illustrated similar reference numerals are given.

The probe tip of FIG. 7, indicated generally at 33', comprises a housing or casing 50' to which is secured a capillary terminal block or "cell" 100 via a reduced diameter, external threaded section 101 of casing 50' and an internal threaded protruding flange section 102 of block 100. A seal 103, such as an O-ring, is located intermediate casing 50' and block 100. Capillary terminal block 100 is provided with a tapered end face 104 having a countersink 105 therein within which a screen assembly 72' is located. Screen assembly 72' is retained in countersink 105 of block 100 by a face plate or member 106 via screws 107, face plate 106 having an opening 108 therein. Screen assembly 72 consists of a molecular screen 74' and a pair of washers or spacers 75' of the type described previously in reference to the embodiment of FIG. 6.

Capillary terminal block or "cell" 100 is preferably constructed of polycarbonate, but may be made of the materials described previously in reference to block 56 of FIG. 6. The block 100 is provided with an elongated slit, groove or countersink 58' which is in communication with countersink 105, and is provided with a pair of spaced passageways 59' and 60' extending from the opposite end of the block 100 and terminating in slit 58', similar to that shown in FIG. 6. Passageways 59' and 60' are of different lengths and each passageway being provided with three different diameter sections 61', 62' and 63', with sections 63' having a curved or tapered inner portion and a threaded outer portion. Capillary tubes 36' and 37' extend through an opening 108 in casing 50, through sections 63' of passageways 59' and 60', into sections 62' and terminate adjacent to section 61 of the passageways. A pair of seals 64' are positioned in the curved end portions of passageway sections 63' and around capillary tubes 36' and 37', seals 64' being constructed as described earlier in reference to FIG. 6. Insulation sleeves 52' terminate in passageway sections 63' adjacent seals 64', with seals 64' being retained by threaded retainer plugs 65', as described above.

The capillary terminal block 100 and face plate 106 are positioned within a mass spectrometer. The sample material to be separated and analyzed migrates through capillary tube 36' and is vaporized as it passes into the mass spectrometer as shown at 90' where it is ionized by an ionizing beam 91', as described previously in reference to the embodiment of FIG. 6, except that the beam 91' impinges directly on the front angled or tapered face, to facilitate the vaporization and ionization of the material components being analyzed.

It has thus been shown that the present invention provides a means to perform electrophoresis directly in the ion source of a mass spectrometer. Inorganic and organic and biological chemicals which are separated from complex mixtures by the electrophoretic process may be analyzed in real-time by the mass spectrometer to yield molecular weights, unique fragmentation data and structural information. This new approach, which utilizes a mass spectrometer as a detector for electrophoresis offers an entirely new dimension to electrophoretic techniques. The interface probe of this invention enables rapid chemical analyses of complex mixtures of polar and biological substances, particularly since the interface probe may be used with an existing mass spectrometer. The invention has particular application or use by hospitals and clinical laboratories in the rapid diagnosis of abnormal metabolic and other disorders. The present interface robe may also be used as a stand-alone, portable, compact electrophoresis unit for field operation.

While the interface probe of this invention has been described and illustrated for directly passing electrophoretically separated chemicals into a mass spectrometer for real-time analysis, the probe is not limited to that use. For example, the probe tip can be located in a detector mecnanism, or have a detector assembly mounted thereon, such that as the separated chemicals reach the end of the probe tip, selected chemicals or amounts can be detected by the detector mechanism for providing a ready readout of the composition of the material being directed through the probe. Spectroscopic data can be substantially simultaneously recorded as each compound passes through the probe.

While a particular embodiment of the invention and specific materials and parameters have been illustrated and described for purposes of illustration and to provide a better understanding of the invention, it is not intended to be exhaustive or to limit the invention to the particular illustrations or embodiments so described. The above embodiments were chosen and described in some detail in order to explain best the principles and the practical application of the subject invention thereby to enable those skilled in the art to utilize the invention in various other embodiments and various modifications as are suitable for the particular use contemplated. Obviously many modifications and variations are possible in light of the above teaching. It is intended that the scope of the invention be defined by the claims appended hereto.

what is claimed is:

1. An electrophoretic mass spectrometric process in which chemical components are separated from complex mixtures and analyzed in real-time to yield molecular weights and structural information of the electrophoretically separated chemicals, the process comprising the steps of:
    directing a quantity of electrically conducting buffer material into a capillary tube;
    directing a mixture to be separated and analyzed into the buffer material in the capillary tube;
    impressing an electrical potential on said capillary tube;
    separating chemicals from the mixture by electrophoresis as the mixture migrates along the interior of the capillary;
    discharging the separated chemicals directly from the capillary tube into an ion source of a mass spectrometer;
    directing an ionizing beam onto the separated chemicals as the separated chemicals discharge from the capillary tube for ionizing the chemicals, and
    analyzing the ionized chemicals in the mass spectrometer.

2. The process of claim 1, additionally including the step of directing a quantity of electrically conducting buffer material through another capillary tube which terminates adjacent the discharge of the separated chemicals from the first-named capillary tube for dissipating heat and for providing continuous electrophoresis separation within the first-mentioned capillary tube.

3. The process of claim 2, wherein said first mentioned capillary tube is made positive with respect to the ground potential and said another capillary is made negative with respect to the ground potential.

4. The process of claim 3, additionally including the step of positioning a molecular screen between the capillary tubes and the mass spectrometer such that the separated chemicals pass through the molecular screen before discharging into the mass spectrometer.

5. The process of claim 1, additionally including the steps of providing a valve mechanism between the capillary tube, a source for the mixture to be separated, a source for the electrically conducting buffer material, and a controlling the valve mechanism so as to periodically inject a quantity of the mixture to be separated into the positively charged capillary tube.

6. The process of claim 1, additionally including the step of providing a data acquisition means to record the analysis data produced by the mass spectrometer 7. The process of claim 1, wherein said mixture to be separated is a complex mixture of polar substances.

8. The process of claim 1, wnerein said mixture to be separated is a complex mixture of biological compounds.

9. An electrophoresis-mass spectrometry interface probe for the separation of complex mixtures of chemicals, comprising:
 at least one capillary tube;
 means for directing buffer material into one end of said capillary tube;
 means for impressing an electrically positive charge on buffer material directed into said capillary tube;
 valve means for controlling flow of buffer material through said capillary tube;
 means for directing sample material to be separated by electrophoresis into said valve means; and
 means for electrically connecting an opposite end of said capillary tube to ground.

10. The interface probe of claim 9, additionally including a casing, said capillary tube being located in said casing, and means secured to said casing for supporting said capillary tube within said casing.

11. The interface probe of claim 9, wherein said supporting means for said capillary tube comprises a block, said block having at least one passageway therethrough, said capillary tube extending at least into said passageway of said block.

12. The interface probe of claim 11, wherein said passageway in said block is threaded, and said capillary tube is retained in said block by a threaded coupling mechanism inserted into said threaded passageway.

13. The interface probe of claim 12, wherein said means for electrically connecting said capillary tube to ground includes an electrical lead connected at a first end to said opposite end of said capillary tube, said electrical lead extending along said casing, past said block, and connected at a second end to an electrical ground means.

14. The interface probe of claim 11, wherein said passageway in said block includes a plurality of different diameter sections, said opposite end of said capillary tube terminating in one of said plurality of different diameter sections of said passageway, and including seal means positioned in another of said plurality of different diameter sections of said passageway and around a section of said capillary tube, and means for retaining said seal means in said passageway.

15. The interface probe of claim 13, wherein said capillary tube is constructed of a multi-layer configuration, and having a central layer of material selected from the group consisting of quartz, sapphire, glass, teflon and polycarbonate; and outer layer of material selected from the group consisting of polyacrylamide, teflon and polystyrene; and an inner layer of material selected from the group consisting of polysilicones, carbowax and polyacrylamide.

16. The interface probe of claim 9, wherein said capillary tube is constructed of a multi-layer configuration, and having a central layer of material selected from the group consisting of quartz, sapphire, glass and teflon; and outer layer of material selected from the group consisting of polyacrylamide, teflon and polystyrene; and an inner layer of material selected from the group consisting of polysilicones, carbowax and polyacrylamide.

17. The interface probe of claim 9, wherein said valve means is of a multi-port type, and having a movable member with a fluid passage therethrough, such that movement of said movable member to one position connects said fluid passage to said sample material directing means, and movement of said movable member to another position connects said fluid passage to said capillary tube and to said buffer material directing means, whereby sample material in said fluid passage is directed into said capillary tube by buffer material for electrophoresis processing within said capillary tube.

18. The interface probe of claim 9, additionally including another capillary tube operatively connected for directing an electrically negative charged buffer material into one end thereof, said another capillary tube having an opposite end located at a location of said opposite end of said first-named capillary tube through which electrically positive charged buffer material is directed.

19. The interface probe of claim 18, additionally including a casing means in which said capillary tubes extend, and means secured to said casing for supporting said opposite end of each of said capillary tubes in a spaced relation.

20. The interface probe of claim 19, wherein said supporting means for said capillary tubes comprises a block having a pair of passageways therethrough, said opposite ends of said capillary tubes being located in said pair of passageways, said passageways having a plurality of different diameter sections, said opposite ends of each of said capillary tubes terminating in one of said plurality of different diameter sections, and seal means positioned in each of said pair of passageways in another of said plurality of different diameter sections and around a section of said capillary tubes, and means for retaining said seal means in each of said passageways.

21. The interface probe of claim 20, wherein said block additionally includes a slit located on an end of said pair of passageways and extending at least between said pair of passageways, and additionally including a molecular screen assembly positioned adjacent said slit in said block, and means having an opening therein for retaining said molecular screen in abutment with said block.

22. The interface probe of claim 21, additionally including means for sealing said block with respect to said casing.

23. The interface probe of claim 21, wherein said block is provided in a tapered end surface in which said molecular screen is assembly is located.

24. The interface probe of claim 21, wherein said molecular screen assembly comprises a molecular screen, constructed from material selected from the group consisting of polycarbonate, teflon, paper and cellulose, and positioned intermediate are pairs of members, each of said pair of members having a centrally located opening therein.

25. The interface probe of claim 19, additionally including a coupling means for securing said probe to a point of use.

26. The interface probe of claim 19, additionally including a coupling mechanism for securing said casing in a mass spectrometer in a vacuum tight arrangement and such that a portion of said casing extends into said mass spectrometer.

27. The combination of a mass spectrometer and interface probe of claim 24, additionally including means for ionizing chemical components of sample material separated by electrophoresis in said first-named capillary tube and discharged into said mass spectrometer.

28. The combination of claim 27, wherein said buffer material directing means includes a reservoir containing electrically positive charged buffer material connected to said valve means, and additionally a reservoir means for directing electrically negative charged buffer material into said another capillary tube, and a high voltage power supply having a positive terminal connected to said reservoir and a negative terminal connected to said reservoir means.

* * * * *